United States Patent [19]

Koga

[11] Patent Number: 4,534,049
[45] Date of Patent: Aug. 6, 1985

[54] FLUORESCENT X-RAY FILM THICKNESS GAUGE

[75] Inventor: Toshiyuki Koga, Gotenba, Japan

[73] Assignee: Kabushiki Kaisha Daini Seikosha, Tokyo, Japan

[21] Appl. No.: 522,041

[22] Filed: Aug. 10, 1983

Related U.S. Application Data

[63] Continuation of Ser. No. 258,518, Apr. 28, 1981, Pat. No. 4,406,015.

[30] Foreign Application Priority Data

Sep. 22, 1980 [JP] Japan .................. 55-135058

[51] Int. Cl.³ .................. G01N 23/20; G21K 1/00
[52] U.S. Cl. .................. 378/050; 378/89; 378/206
[58] Field of Search .......... 378/44, 45, 86, 88, 378/206, 50, 89; 250/491.1

[56] References Cited

U.S. PATENT DOCUMENTS

| | | | |
|---|---|---|---|
| 2,455,928 | 12/1948 | Hawks | 250/64 |
| 2,942,113 | 6/1960 | Handel | 250/83.6 |
| 3,705,305 | 12/1972 | Fischer | 250/83.3 D |
| 3,729,632 | 4/1973 | Cho et al. | 250/83.3 D |
| 3,918,793 | 11/1975 | Kraft | 350/91 |
| 4,162,528 | 7/1979 | Maldano et al. | 364/563 |
| 4,178,511 | 12/1979 | Hounsfield et al. | 250/445 T |
| 4,178,513 | 12/1979 | Dubois | 250/491 |
| 4,195,229 | 3/1980 | Suzuki | 250/445 T |
| 4,406,015 | 9/1983 | Koga | 378/50 |

FOREIGN PATENT DOCUMENTS

| | | |
|---|---|---|
| 7705443 | 11/1977 | Netherlands . |
| 249401 | 6/1948 | Switzerland . |
| 854762 | 11/1960 | United Kingdom . |
| 899291 | 6/1962 | United Kingdom . |
| 2040037 | 8/1980 | United Kingdom . |

OTHER PUBLICATIONS

Instruments and Control Systems 41, (Jan. 1, 1968), p. 59, General Electric Co., advertisement.
Proceedings of the Third International Symposium on Research Materials for Nuclear Measurements, vol. 102, (1972), No. 3, pp. 599-610.
Journal of Physics E: Scientific Instruments, vol. 6, 1973, No. 8, Aug., pp. 781-784.

Primary Examiner—Alfred E. Smith
Assistant Examiner—T. N. Grigsby
Attorney, Agent, or Firm—Robert E. Burns; Emmanuel J. Lobato; Bruce L. Adams

[57] ABSTRACT

A fluorescent X-ray film thickness gauge comprises an X-ray tube for irradiating X-rays along an X-ray axis to a sample having a film coating whose thickness is to be measured, a detector for detecting fluorescent X-rays emitted from the sample, viewing means including a mirror for enabling an observer to view along the X-ray axis a target spot on the sample at which the X-ray beam is to be directed, and a collimator for collimating the X-rays into an X-ray beam and directing the X-ray beam along the X-ray axis to the target spot on the sample. In a preferred embodiment, the collimator and mirror are both mounted on a displaceable shutter member which is displaceable between a viewing position, in which the mirror is positioned along the X-ray axis to enable viewing of the target spot on the sample while the shutter member blocks the X-rays from irradiating the sample, and an irradiating position, in which the collimator is positioned along the X-ray axis to direct the X-ray beam to the target spot on the sample.

14 Claims, 15 Drawing Figures

FLUORESCENT X-RAY FILM THICKNESS GAUGE

RELATED APPLICATION

This application is a continuation of application Ser. No. 258,518 filed Apr. 28, 1981 and now U.S. Pat. No. 4,406,015.

BACKGROUND OF THE INVENTION

The present invention relates generally to fluorescent X-ray film thickness gauges, and more particularly to fluorescent X-ray film thickness gauges having means for irradiating X-rays along an X-ray axis to a precise spot on a sample and for enabling an observer to view along the X-ray axis the spot on the sample at which the X-rays are to be directed.

In recent years, there has been an increasing demand for an accurate and reliable technique for measuring the thickness of film coatings in the electronic industry. For example, the need for such film thickness measurements is commonplace in the fabrication of integrated circuits, electric connections, printed circuit boards and in numerous other applications where a film coating of one material is applied on a base material. In general, the film coating is plated, coated, evaporated, sputtered or otherwise deposited on the base material, and with the highly developed fabrication techniques in use today, the film coatings are smaller in area, and therefore more difficult to measure, than ever before.

Figure 1:
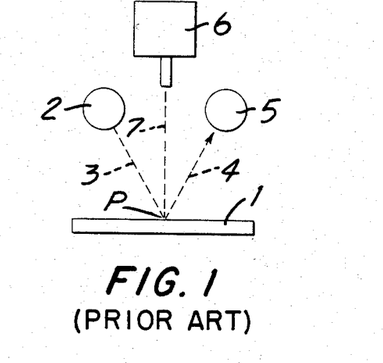
FIG. 1 is an explanatory diagram of a conventional fluorescent X-ray film thickness gauge.
Figure 2:
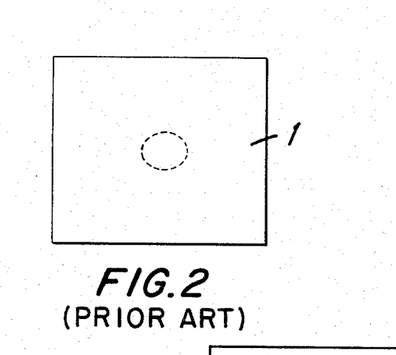
FIG. 2 is an enlarged plan view showing the elliptical shape of an X-ray beam point irradiated on a sample by the gauge of FIG. 1.

It is known in the art to use fluorescent X-ray film thickness gauges for measuring film thicknesses and such gauges are advantageous since they perform non-contact and nondestructive measurement. The conventional type fluorescent X-ray film thickness gauge is shown in FIGS. 1-2 in conjunction with a sample 1 having a film whose thickness is to be measured. The gauge comprises an X-ray tube 2 positioned above the sample 1 for irradiating X-rays along an X-ray axis 3 to a measuring point P on the sample and in response to such irradiation, the sample 1 emits fluorescent X-rays 4 from the measuring point P. A detector 5 is positioned to receive the fluorescent X-rays 4 emitted by the sample 1 for developing an output signal proportional to the amount of the fluorescent X-rays for use in measuring the film thickness. As known in the art, the principle of fluorescent X-ray measurement is based on the fact that when a material is irradiated by X-rays, fluorescent X-rays are emitted having wavelengths or energies characteristic of the elements contained in the material.

As shown in FIG. 1, in order to determine the point P on the sample 1 which is to be irradiated by X-rays, viewing means 6, which typically comprises a microscope and projector, is positioned above the sample so that an observer may view along an optical axis 7 the spot on the sample to be irradiated. However, since the optical axis 7 of the viewing means 6 does not coincide with the X-ray axis 3 of the X-ray tube 2, the shape of the target spot on the sample 1 which is irradiated by the X-rays differs from the shape of the target spot as viewed by the viewing means. In other words, since the surface of the sample 1 is not irradiated by the X-ray beam in a direction normal to the surface but rather is irradiated at an inclined angle relative to the normal, the shape of the irradiating point of the X-ray beam on the sample 1 is elliptical rather than circular as shown by the dotted line representation of the irradiating point, on an enlarged scale, in FIG. 2.

This discrepancy between the shape of the target spot as viewed by the observer through the viewing means 6 and as irradiated by the X-ray tube 2 can lead to measurement errors, particularly when measuring the film thickness of very small coating areas and/or of precisely shaped components such as are oftentimes found on integrated circuits. Since the target spot to be irradiated is determined by viewing through the viewing means 6 which presents to the observer a circular target area, and since the spot actually irradiated by the X-ray tube 2 is an elliptical area, the neighboring portions of the target area are also irradiated thereby leading to the likelihood of inaccurate measurements. This is so even if the X-ray beam is made as thin as possible since in all cases, the irradiating point will be elliptical rather than circular due to the inclination of the X-ray axis 3 relative to the optical axis 7. Another drawback of the conventional gauge is that if the sample 1 is moved vertically upward during measuring, the shape of the irradiating point becomes even more elliptical and the measuring accuracy becomes correspondingly less accurate.

SUMMARY OF THE INVENTION

It is, therefore, an object of the present invention to provide a fluorescent film thickness gauge which overcomes the aforementioned drawbacks and disadvantages of prior art gauges.

Another object of the present invention is to provide a fluorescent X-ray film thickness gauge in which the irradiating point of the X-ray beam can be precisely and accurately positioned on the target spot on the sample.

A further object of the present invention is to provide a fluorescent X-ray film thickness gauge in which an observer can view along the X-ray axis the target spot on the sample at which the X-ray beam is to be directed for irradiating the sample.

A still further object of the present invention is to provide a fluorescent X-ray film thickness gauge in which the shape of the irradiating point of the X-ray beam which irradiates the sample is the same as the shape of the target spot on the sample which is viewed by the observer.

Still another object of the present invention is to provide a fluorescent X-ray film thickness gauge which is capable of accurately measuring very small film coating areas with high precision and accuracy.

The above and other objects of the invention are carried out by a fluorescent X-ray film thickness gauge having an X-ray tube for irradiating X-rays along an X-ray axis to a sample having a film whose thickness is to be measured, a detector for detecting fluorescent X-rays emitted from the sample, viewing means for enabling an observer to view along the X-ray axis a target spot on the sample at which the X-ray beam is to be directed, and a collimator for collimating the X-rays into an X-ray beam and directing the X-ray beam along the X-ray axis to the target spot on the sample.

DETAILED DESCRIPTION OF PREFERRED EMBODIMENT OF THE INVENTION

Figure 3:
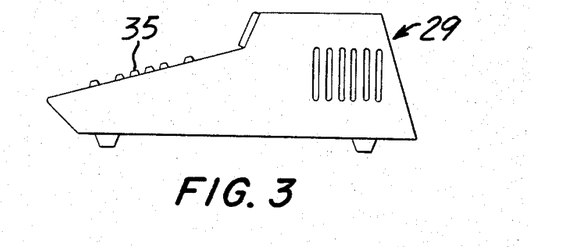
FIG. 3 is a side elevational view of a controller used in the fluorescent X-ray film thickness gauge of the present invention.
Figure 4:
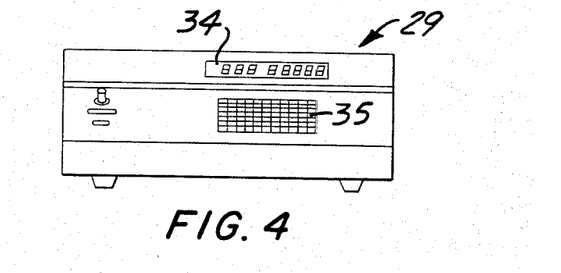
FIG. 4 is a front elevational view of the controller shown in FIG. 3.
Figure 5:
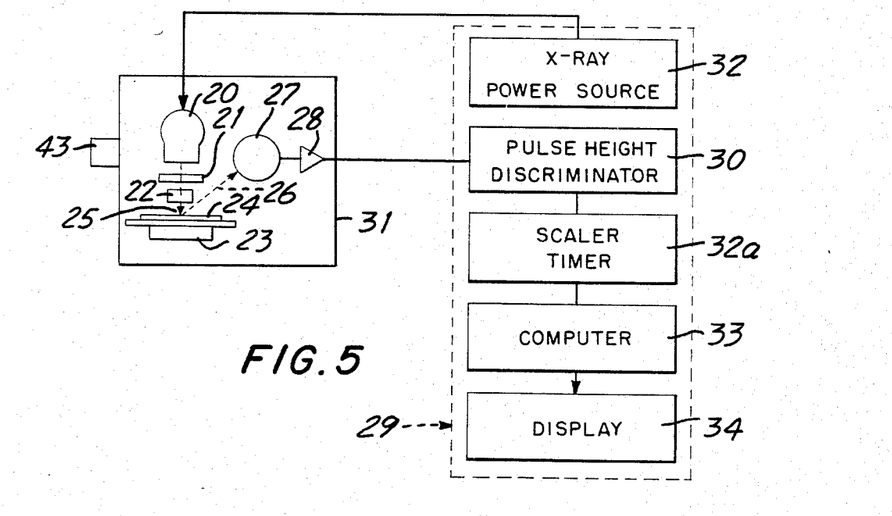
FIG. 5 is an explanatory diagram showing the overall construction of a fluorescent X-ray film thickness gauge comprised of a controller and measurement head according to the present invention.

One embodiment of a fluorescent X-ray film thickness gauge according to the present invention will be described in conjunction with FIGS. 3–13. As shown in FIG. 5, the fluorescent X-ray film thickness gauge comprises a controller 29 connected to control a measurement head 31. The measurement head 31 comprises an X-ray tube 20 for irradiating X-rays along an X-ray axis to a sample 24 which is positioned on a sample holder 23. A shutter member 21 and a collimator 22 are disposed along the X-ray axis between the X-ray tube 20 and the sample holder 23 for controlling the application of X-rays to the sample as described in more detail hereafter. In operation, the X-ray tube 20 irradiates X-rays along an X-ray axis and the collimator 22 collimates the X-rays into an X-ray beam 25 which irradiates a point on the sample 24 causing the sample to emit fluorescent X-rays 26. The fluorescent X-rays 26 are detected by a detector 27 which converts the detected fluorescent X-rays into a corresponding electrical detection signal which is proportional to the intensity of the detected fluorescent X-rays. The detection signal is amplified by an amplifier 28 and fed to the controller 29.

The controller 29 controls the operation of the measurement head 31 and comprises an X-ray power source 32 for supplying power to the X-ray tube 20, a pulse height discriminator 30 which receives and discriminates by pulse height the electrical detection signal output from the measurement head 31 and applies the discriminated signals to a scaler timer 32a which is connected to a micro computer 33 for processing and computing information pertaining to the film coating on the sample 24. The computer 33 is connected to a digital display 34 which displays data in digital form. As shown in FIGS. 3 and 4, the controller 29 includes a keyboard 35 for inputting data for use by the micro computer 33.

Figure 6:
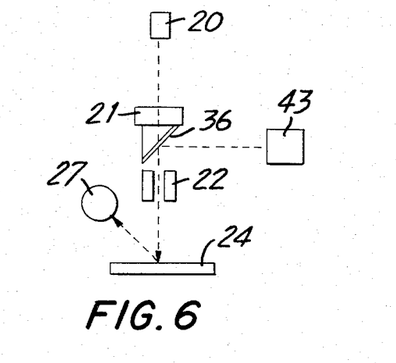
FIG. 6 is an explanatory diagram of the measurement head shown in FIG. 5.
Figure 7:
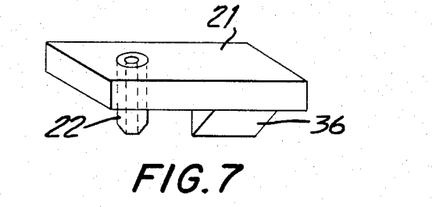
FIG. 7 is a perspective view of a shutter assembly which is diagrammatically shown in FIG. 6.

FIG. 6 is an explanatory diagram showing the basic mode of operation of the measurement head and FIG. 7 is a perspective view of the shutter assembly which is shown diagrammatically in FIG. 6. The shutter assembly is an integral structure comprised of the shutter member 21, the collimator 22 and a mirror 36. The collimator 22 and the mirror 36 project downwardly from the underside of the shutter member 21 and are spaced apart from each other in the manner shown in FIG. 7. The shutter assembly is displaceable along a horizontal axis between an irradiating position, in which the collimator 22 is aligned along the X-ray axis to collimate the X-rays from the X-ray tube 20 into an X-ray beam for irradiating the sample, and a blocking position, in which the shutter member 21 blocks the transmission of X-rays to the sample and in which the mirror 36 is positioned along the X-ray axis so as to enable an observer to view along the X-ray axis the target spot on the sample at which the X-ray beam is to be directed. The blocking position of the shutter member 21 corresponds to the viewing position thereof, i.e., the position which effects blocking of the X-rays and permits viewing of the sample.

As shown in FIG. 6, when the shutter member 21 is in the blocking or viewing position, light reflected from the sample 24 travels along the X-ray axis to the mirror 36 and is reflected by the mirror along an optical axis to a microscope 43 to enable viewing of the sample on an enlarged scale. The mirror 36 and the microscope 43 comprise viewing means for enabling an observer to view the sample. By such a construction, the observer, using the viewing means, can suitably position the sample 24 so that the desired target spot on the sample is located along the X-ray axis. When it is desired to irradiate the target spot on the sample, the shutter member 21 is displaced from the blocking or viewing position to the irradiating position thereby aligning the collimator 22 with the X-ray axis so that the X-rays emitted by the X-ray tube 20 are collimated into an X-ray beam and directed along the X-ray axis to the target spot on the sample. Thus in accordance with the invention, the optical axis coincides with the X-ray axis and both axes intersect the sample 24 in a direction normal to the surface of the sample so that the shape of the target spot on the sample and the shape of the irradiating point of the X-ray beam on the sample are both circular. As a consequence, very small film coating areas can be measured with high precision and accuracy.

Figure 10:
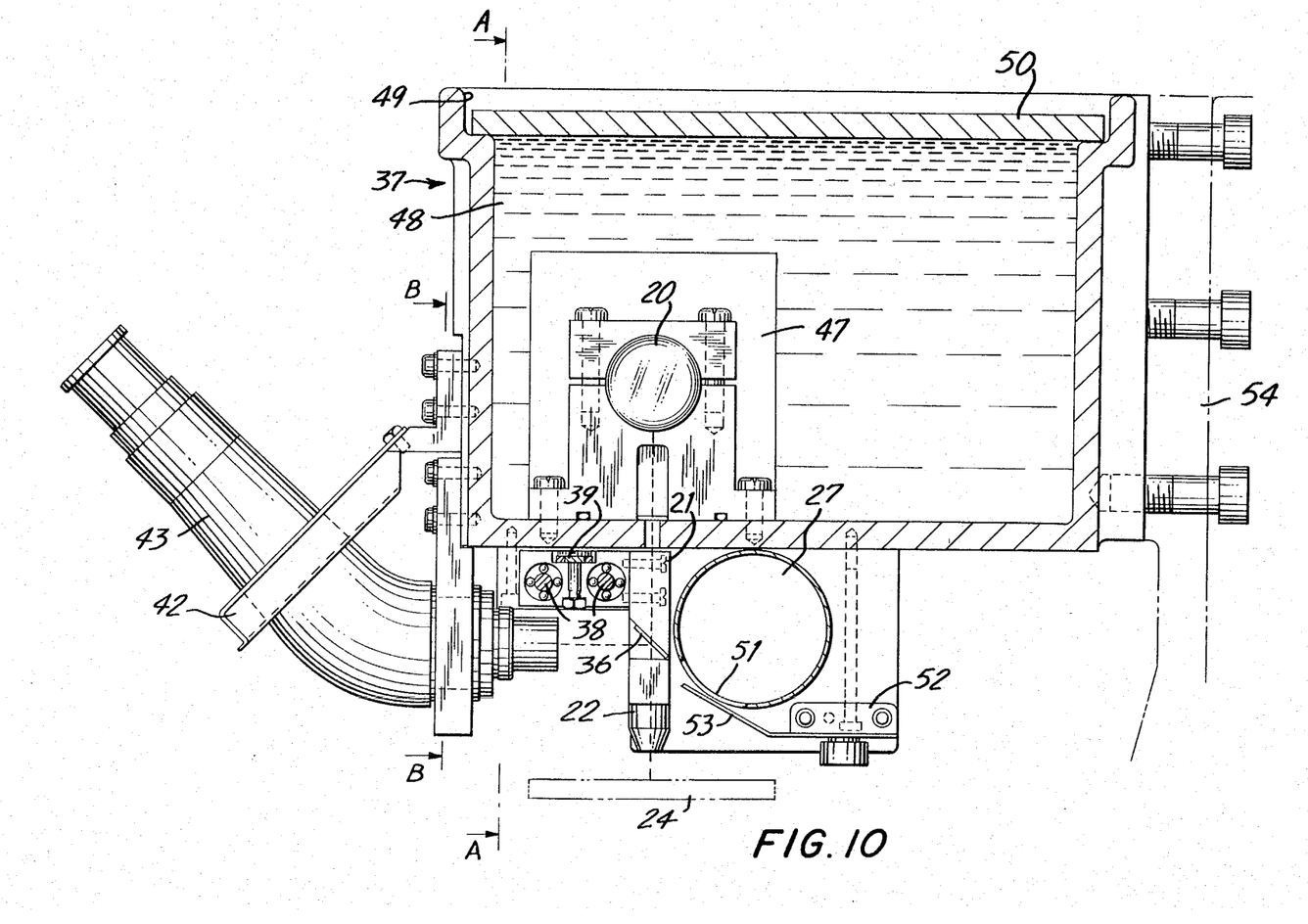
FIG. 10 is an enlarged cross-sectional view of a part of the measurement head shown in FIG. 8.
Figure 11:
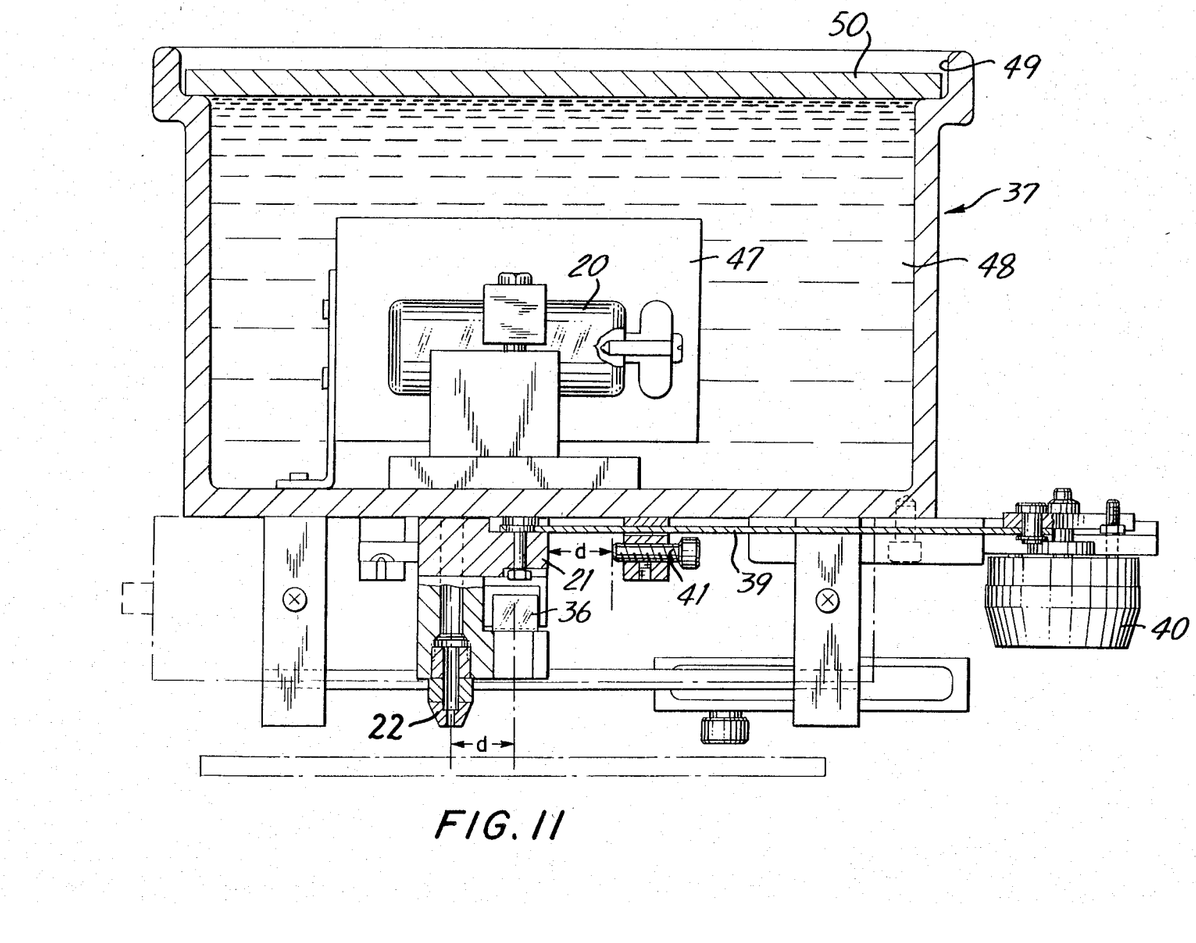
FIG. 11 is a cross-sectional view taken along the line A—A of FIG. 10.
Figure 12:
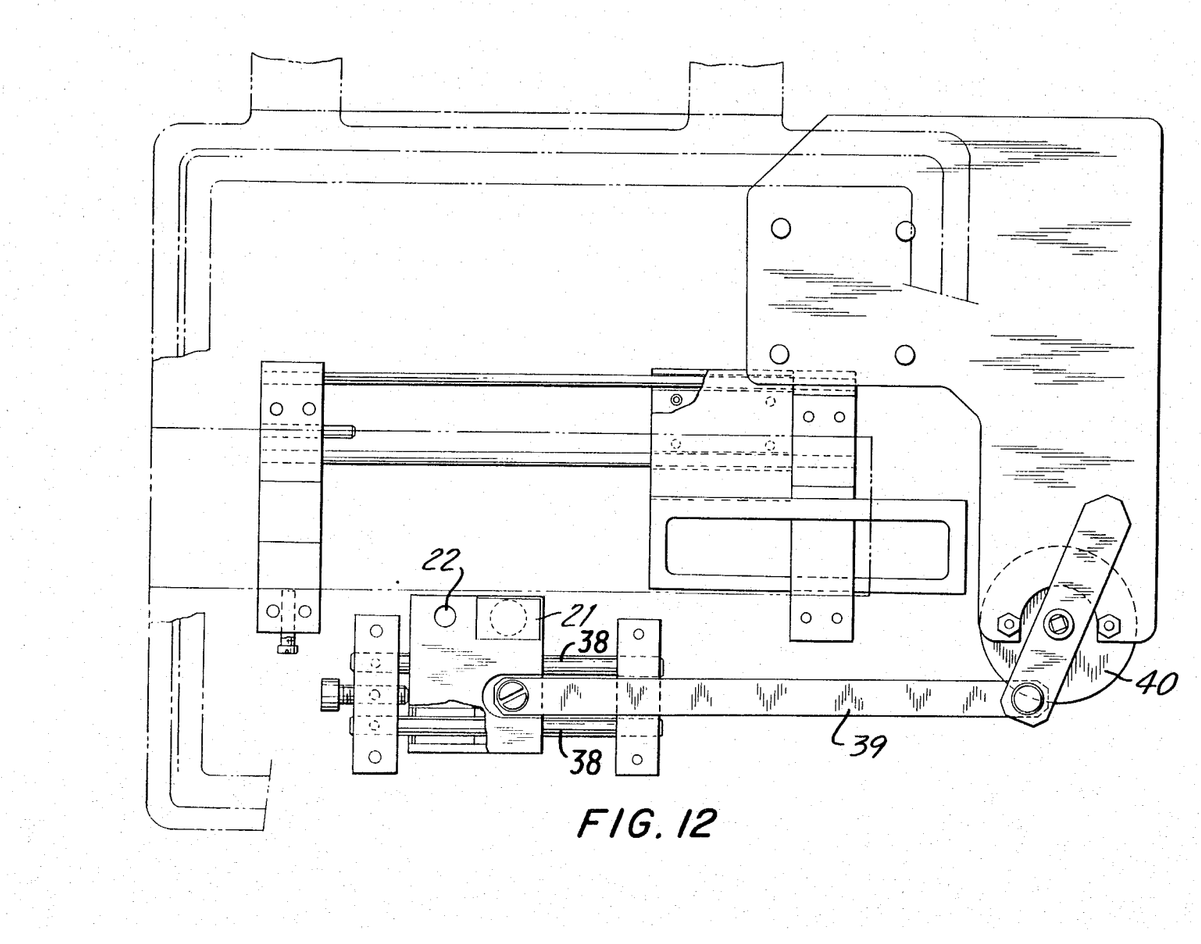
FIG. 12 is a plan view of the part of the measurement head shown in FIG. 10.

The structural configuration of the measurement head 31 will now be described in more detail with reference to FIGS. 8–13. As shown in FIGS. 10 and 12, the shutter member 21 is mounted for sliding movement along guide rails 38 provided at the bottom portion of a tank 37. Actuating means comprising a guide plate 39 secured to the shutter member 21 and a rotary solenoid 40 secured to the bottom portion of the tank 37 effect sliding displacement of the shutter assembly along the guide rails 38 between the blocking or viewing position and the irradiating position. As shown in FIG. 11, an adjustable stopper screw 41 is positioned to abut with the shutter member 21 when the shutter member moves rightward to thereby determine one stop position of the shutter member. When properly adjusted, the distance d between the axis of the collimator 22 and the optical axis of the mirror 36 equals the distance d between the stopper screw 41 and the end face of the shutter member 21 which abuts against the stopper screw. In this manner, when the rotary solenoid 40 is actuated, the shutter member 21 moves either leftward or rightward a distance d so as to alternately position the mirror 36 or the collimator 22 along the X-ray axis.

When the shutter member 21 is in the blocking or viewing position shown in FIG. 11, the upper surface of the shutter member blocks the transmission of X-rays along the X-ray axis and positions the mirror 36 along the X-ray axis whereby light reflected from the sample 24 travels back along the X-ray axis and is reflected by the mirror 36 along the optical axis on which is positioned the microscope 43. In this position of the shutter member 21, the optical axis and the X-ray axis coincide in the region from the mirror 36 to the sample 24 thereby enabling an observer to view along the X-ray axis the target spot on the sample at which the X-ray beam is to be directed. This arrangement can best be seen in FIG. 10. When the rotary solenoid 40 is actuated to shift the shutter member 21 rightward a distance d to position the shutter member in the irradiating position, the shutter member 21 abuts the stopper screw 41 thereby aligning the collimator 22 with the X-ray axis so that X-rays emitted from the X-ray tube 20 are collimated into an X-ray beam and directed along the X-ray axis to the target spot on the sample.

Figure 13:
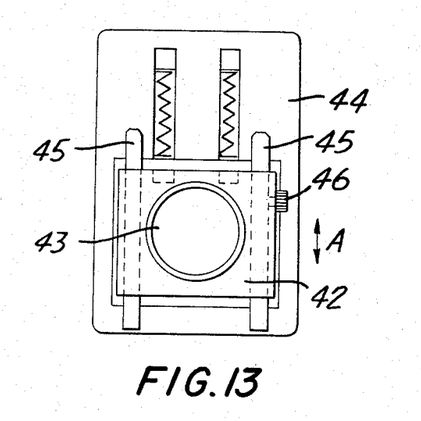
FIG. 13 is a cross-sectional view taken along the line B—B of FIG. 10.

The details of the microscope 43 are shown in FIGS. 10 and 13. The microscope 43 is secured to a holder 42 attached to the sidewall portion of the tank 37. The holder 42 is slidable along guide shafts 45 mounted on a base plate 44 which is secured to the side of the tank 37. In this manner, the holder 42 is slidable in the direction of the double headed arrow A and the holder can be selectively positioned by means of a turnable adjusting screw 46. Such an arrangement enables precise adjustment of the microscope 43 so as to align the optical axis of the microscope with the X-ray axis of the X-ray tube 20 and to bring the two axes into coincidence.

Figure 8:
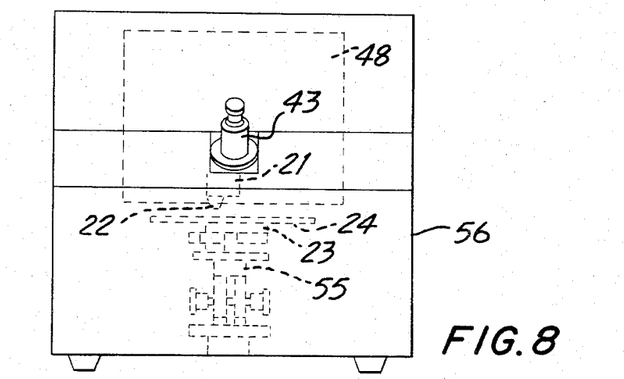
FIG. 8 is a front elevational view of the measurement head of a fluorescent X-ray film thickness gauge according to the present invention.
Figure 9:
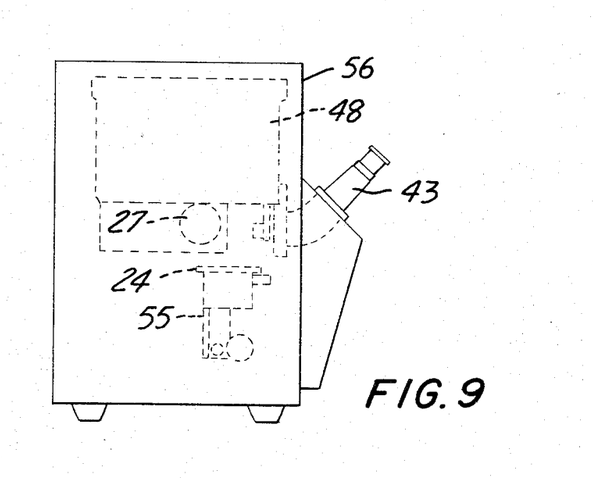
FIG. 9 is a side elevational view of the measurement head shown in FIG. 8.

As shown in FIGS. 8 and 9, the microscope 43 projects from the center portion of a casing 56. The sample holder 23 is mounted on positioning means 25 which is of conventional construction and which suitably positions the sample holder 23 so that the desired target spot on the sample 24 can be brought into focus and enlarged by the microscope 43. With this arrangement, the microscope 43 can focus on a small target area on the order of about 0.3 mm$\phi$.

The X-ray tube 20 is mounted within the tank 37 in an enclosure 47. The tank 37 is filled with an insulating oil 48, and a cover plate 50 is mounted on an upper rim portion 49 of the tank 37. The detector 27 is positioned at the lower part of the tank 37. A filter guide 52 is positioned adjacent the detector 27 for releasably holding a filter 53 in a position wherein the filter extends across the opening 51 of the detector 27. Different filters 53 comprised of different materials can be interchangeably mounted on the filter guide 52 depending on the material composition of the sample being measured. The filter 53 is positioned so that the fluorescent X-rays emitted from the sample 24 must pass through the filter in order to travel through the opening 51 for detection by the detector 27.

Figure 14:
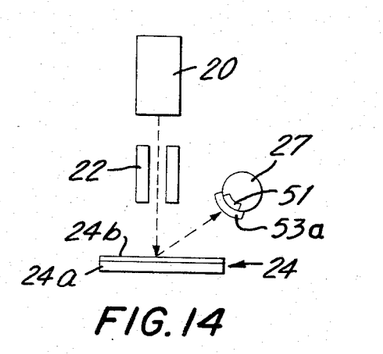
FIGS. 14 and 15 are explanatory and perspective views, respectively, of a detector and filter assembly used with the fluorescent X-ray film thickness gauge of the present invention.
Figure 15:
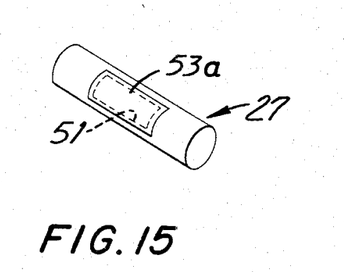

FIGS. 14 and 15 show an embodiment of detector and filter assembly in which the filter 53a is comprised of cobalt which has the property of filtering out or eliminating fluorescent X-rays of copper and passing fluorescent X-rays of the nickel spectrum. Such an arrangement could be used for measuring the film thickness of a nickel coating 24b on a copper base 24a and the fluorescent X-rays emitted from the sample 24 would be filtered by the cobalt filter 53 so that only those of the nickel spectrum would pass and be counted by the detector 27. For clarity, the shutter member 21 and the mirror 36 have been omitted from the diagramatic showing of the measurement head in FIG. 14 which is shown in its irradiating mode.

Fluorescent X-ray film thickness gauges constructed according to the principles of the present invention enable an observer to view along the X-ray axis the spot on the sample at which the X-ray beam is to be directed since the optical axis of the viewing means coincides with the X-ray axis of the X-ray tube in the vicinity of the sample. This enables the X-ray measuring point for the sample to be both observed and determined from the same direction as the X-ray axis of the X-ray tube. Therefore very small measuring areas, such as on the order of about 0.3 mm$\phi$, can be measured. Moreover, the shape of the X-ray beam which is irradiated on the sample is circular in shape thereby eliminating mis-irradiation and mis-measurement of the sample which could otherwise occur if the X-ray beam were elliptical in shape.

Obvious modifications of the aforedescribed fluorescent X-ray film thickness gauges will become apparent to those ordinarily skilled in the art and the present invention is intended to cover all such obvious changes and modifications which fall within the scope and spirit of the appended claims.

What I claim is:

1. In a fluorescent X-ray film thickness gauge having an X-ray tube for irradiating X-rays along an X-ray axis to a sample having a film whose thickness is to be measured, and a detector for detecting fluorescent X-rays emitted from the sample: viewing means for enabling an observer to view along the X-ray axis the spot on the sample at which the X-ray beam is to be directed, the viewing means including a mirror positionable along the X-ray axis at a predetermined position to enable viewing of the spot on the sample, the mirror being displaceable into and out of the predetermined position; and collimating means for collimating the X-rays into an X-ray beam and directing the X-ray beam along the X-ray axis to the said spot on the sample.

2. A gauge according to claim 1 wherein the viewing means further includes a microscope coacting with the mirror to enable viewing of the spot on the sample on an enlarged scale.

3. A gauge according to claim 1 further including a displaceable shutter member having mounted thereon the collimating means; and actuating means for displacing the shutter member to an irradiating position in which the collimating means is positioned along the X-ray axis to enable the X-ray beam to be irradiated on the spot on the sample and for displacing the shutter member to a blocking position in which the shutter member blocks the transmission of X-rays along the X-ray axis.

4. A gauge according to claim 1; further comprising a displaceable shutter member having mounted thereon the collimating means and the mirror; and actuating means for displacing the shutter member to a viewing position in which the mirror is positioned in its predetermined position along the X-ray axis to enable viewing of the spot on the sample and for displacing the shutter member to an irradiating position in which the collimating means is positioned along the X-ray axis to enable the X-ray beam to be irradiated on the spot on the sample.

5. A gauge according to claim 4; wherein the shutter member includes means for blocking the transmission of X-rays along the X-ray axis when the shutter member is in the viewing position.

6. A gauge according to claim 5; wherein the shutter member, mirror and collimating means comprise an integral structure.

7. A gauge according to claim 6; wherein the shutter member has an elongate shape and has an upper portion facing toward the X-ray tube and a lower portion facing toward the sample, the mirror and collimating means both extending downwardly from the lower portion of the shutter member.

8. A gauge according to claim 7; wherein the upper portion of the shutter member has a substantially flat shape.

9. In a fluorescent X-ray film thickness gauge having an X-ray tube for irradiating X-rays along an X-ray axis to a sample having a film whose thickness is to be measured, and a detector for detecting fluorescent X-rays emitted from the sample: viewing means including a mirror for enabling an observer to view along the X-ray axis the spot on the sample at which the X-ray beam is to be directed; collimating means for collimating the X-rays into an X-ray beam and directing the X-ray beam along the X-ray axis to the said spot on the sample; and a displaceable shutter member having mounted thereon both the collimating means and the mirror and being displaceable to a viewing position in which the mirror is positioned along the X-ray axis to enable viewing of the spot on the sample and to an irradiating position in which the collimating means is positioned along the X-ray axis to enable the X-ray beam to be irradiated on the spot on the sample.

10. A gauge according to claim 9; wherein the shutter member includes means for blocking the transmission of X-rays along the X-ray axis when the shutter member is in the viewing position.

11. A gauge according to claim 9; wherein the shutter member, mirror, and collimating means comprise an integral structure.

12. A gauge according to claim 11; wherein the shutter member has an elongate shape and has an upper portion facing toward the X-ray tube and a lower portion facing toward the sample, the mirror, and the collimating means both extending downwardly from the lower portion of the shutter member.

13. A gauge according to claim 9; wherein the mirror and collimating means are mounted in spaced-apart relation on the shutter member in the direction of displacement of the shutter member.

14. A gauge according to claim 13, wherein the collimating means extends completely through the shutter member to permit the X-ray beam to pass therethrough when the shutter member is in the irradiating position; and the shutter member has means for blocking the transmission of the X-ray beam along the X-ray axis when the shutter member is in the viewing position.

* * * * *